(12) United States Patent
Brem

(10) Patent No.: US 8,534,575 B2
(45) Date of Patent: Sep. 17, 2013

(54) SPRAY HEAD AND SPRAYING DEVICE HAVING PRESSURIZED GAS LINE

(75) Inventor: William Brem, Muri (CH)

(73) Assignee: Medmix Systems AG, Rotkreuz (CH)

( * ) Notice: Subject to any disclaimer, the term of this patent is extended or adjusted under 35 U.S.C. 154(b) by 175 days.

(21) Appl. No.: 13/124,789

(22) PCT Filed: Oct. 23, 2009

(86) PCT No.: PCT/CH2009/000341
§ 371 (c)(1),
(2), (4) Date: Apr. 18, 2011

(87) PCT Pub. No.: WO2010/048734
PCT Pub. Date: May 6, 2010

(65) Prior Publication Data
US 2011/0253806 A1    Oct. 20, 2011

(30) Foreign Application Priority Data
Oct. 30, 2008   (CH) ....................................... 1706/08

(51) Int. Cl.
*B05B 7/00*     (2006.01)
*B05B 1/14*     (2006.01)
*A61M 11/00*    (2006.01)

(52) U.S. Cl.
USPC ........... 239/422; 239/296; 239/306; 239/418; 239/419.3; 239/590.5; 222/137; 222/145.5; 222/145.6; 604/82

(58) Field of Classification Search
USPC ............ 239/8, 290, 296, 303, 304, 306, 307, 239/335, 398, 418, 419, 419.3, 422, 423, 239/424, 425, 428, 432, 589, 590, 590.5; 222/129, 132, 134, 135–137, 145.1, 145.5, 222/145.6; 604/82, 191
See application file for complete search history.

(56) References Cited

U.S. PATENT DOCUMENTS

| 5,605,541 | A | | 2/1997 | Holm |
| 5,665,067 | A | * | 9/1997 | Linder et al. .................... 604/82 |
| 5,740,965 | A | * | 4/1998 | Miyagi et al. ................. 239/423 |
| 6,062,492 | A | | 5/2000 | Tudor et al. |
| 2003/0226910 | A1 | | 12/2003 | Anderson |
| 2006/0189944 | A1 | * | 8/2006 | Campbell et al. ............. 604/191 |

FOREIGN PATENT DOCUMENTS

WO          97/48496 A1    12/1997

* cited by examiner

*Primary Examiner* — Darren W Gorman
(74) *Attorney, Agent, or Firm* — Sughrue Mion, PLLC

(57) ABSTRACT

A spraying device having a spray head for spraying at least one component comprises at least one substance component duct (6, 6'; 20), the component outlet (8, 8'; 23, 23') of which leads out of a spray head tip (7). An annular duct (12) for a pressurized gas surrounds the at least one component duct (6, 6'; 20) at least partially in the longitudinal direction and leads out of the spray head (5) at the spray head tip (7). A pressurized gas supply duct (13) is provided for introducing pressurized gas at the annular duct (12). The annular duct (12) has a plurality of ribs (16, 16'), which divide the annular duct (12) at least in the region of the spray head tip (7) into pressurized gas outlet ducts (17, 17') that are separated from each other.

19 Claims, 9 Drawing Sheets

SPRAY HEAD AND SPRAYING DEVICE HAVING PRESSURIZED GAS LINE

CROSS REFERENCE TO RELATED APPLICATIONS

This application is a National Stage of International Application No. PCT/CH2009/000341 filed Oct. 23, 2009, which claims priority from Swiss Patent Application No. 1706/08 filed Oct. 30, 2008, the contents of all of which are incorporated herein by reference in their entirety.

The present invention relates to a spraying device and a spray head for a spraying device for spraying at least one substance or component by pressurized gas, in particular a spray head and a spraying device in which individual components are mixed together by means of the pressurized gas after they exit the spray head.

PRIOR ART

The prior art discloses spraying devices which, for example, are used in treatment procedures in the field of medicine. With the aid of the spraying devices, it is possible, for example, for an adhesive, such as fibrin or thrombin, to be applied to a treatment surface without touching the latter. Such methods are used, for example, to treat wounds or to stop bleeding. The substances applied with the spraying device are often stored in the form of separate components, for example in a double cartridge or double syringe, and the components are mixed with one another only at the time of use. The mixing of the components can take place directly after the individual components emerge from a spray head of the spraying device and upon atomization of the individual components. It is also possible for the components to be mixed in a mixing channel inside the device and to be sprayed immediately. In this case, however, clogging or soiling can occur inside the spraying device. The components are discharged from the spray head and atomized into individual droplets by a gas stream directed simultaneously toward the components. The gas stream transports the mixed components onto a treatment site. Care has to be taken to ensure that the spray pattern has a uniformly fine droplet size and that the components are mixed together as thoroughly as possible. For some applications, it is necessary to transport the mixed components in as narrow a focus as possible. It is also desirable to be able to spray highly viscous components using the least possible amount of pressurized gas.

U.S. Pat. No. 5,605,541, for example, discloses a spraying device in which the individual components and a gas are conveyed in separate ducts into a spray head. The gas duct is arranged centrally in the spray head, and the component ducts extend in a ring shape around the gas duct. The ducts open out in a common plane at the tip of the spray head such that, when the components and the gas are discharged, mixing of the components takes place. In this spraying device, the components emerge from the spray head in a ring shape over a large surface area. The components and the pressurized gas are not output in a coordinated way and in a defined direction, and the distance between the pressurized gas duct and the outer component duct is very great, such that it is not really possible to guarantee complete coverage of the components by the pressurized gas.

It is therefore an object of the present invention to make available a spray head and a spraying device that permit uniform mixing of components and uniformly fine droplet formation, provide targeted and narrow focussing of the components and of the mixture, require little pressurized gas for spraying, avoid clogging or soiling of the spray head, and are suitable for highly viscous components.

DISCLOSURE OF THE INVENTION

According to the present invention, a spray head for a spraying device for spraying at least one substance or component is provided. The spray head comprises at least one substance or component duct, in which the substance or component is guided. Preferably, at least two component ducts are provided, one for each spray component. The component ducts have component outlets, which are arranged next to each other and open out from a tip of the spray head. The component outlets are preferably provided close to each other on the spray head tip. For example, the distance between the two component outlets corresponds approximately to the dimension of their diameters. The component ducts can be provided lying farther apart. The component ducts inside the spray head are preferably routed parallel to and alongside each other in the spraying direction. However, the component ducts can also be routed independently of each other through the spray head, as long as their component outlets come to lie close to each other at the spray head tip. The different spray components are introduced into the component ducts from containers, for example a double cartridge or a double syringe.

The spray head further comprises an annular duct for a pressurized gas, which annular duct at least partially surrounds the component ducts in the longitudinal direction and leads out from the spray head at the spray head tip. It is sufficient if the pressurized gas surrounds the component ducts in an area at the spray head tip and close to the spray head tip. However, it is also possible for the annular duct to extend in the longitudinal direction along the component ducts. The component ducts are preferably surrounded concentrically by the annular duct. It must be ensured that the outlet of the annular duct comes to lie on the spray head tip close to the component outlets. For this purpose, the annular duct can advantageously be designed tapering in the direction of the component outlets. By means of the concentric arrangement of the outlet of the annular duct, the component ducts are each spaced apart at the same distance from an area of the annular duct.

A pressurized gas supply duct is provided for introducing pressurized gas into the annular duct. The pressurized gas supply duct is preferably provided laterally on the spray head and has an attachment for a device that generates pressurized gas. It is also possible to provide the pressurized gas supply duct parallel to the annular duct, such that the pressurized gas is not introduced laterally into the annular duct but instead in the longitudinal direction of the spraying device. Gas cartridges or pumps, for example, can be used to generate pressurized gas. For most applications, pressurized air can be used as pressurized gas. When the spray head or the spraying device is being used, the spray components are discharged from the component ducts and the pressurized gas from the annular duct simultaneously.

According to the present invention, the annular duct has a plurality of webs, which divide the annular duct, at least in the area of the spray head tip, into pressurized gas outlet ducts that are separate from one another. The annular duct is thus divided into individual pressurized gas outlet ducts, which are arranged in a ring shape around the component ducts. The webs can be of different length and width, such that different pressurized gas outlet ducts can be formed. The individual pressurized gas outlet ducts directly adjoin the annular duct. A pressurized gas introduced through the pressurized gas supply duct flows through the annular duct and is distributed to the individual pressurized gas outlet ducts. In the longitudinal direction, the webs can be arranged in the direction of the tip, e.g. widened, in such a way that the pressurized gas ducts narrow in the direction of the tip. Moreover, a different width of the webs can provide a different spacing of the pressurized gas outlet ducts at the spray head tip, and pressurized gas outlet ducts of different diameters can be obtained.

By means of a spray head according to the invention, with an annular duct divided by several webs into separate pressurized gas outlet ducts, it is possible to reduce the quantity of gas needed to atomize the components. The stream of pressurized gas can be arranged in a targeted and definitive manner relative to the component ducts. Moreover, the distribution of the quantity of pressurized gas can be adapted to a corresponding component or a combination of components. This permits uniform mixing of the components and an atomization with a uniformly fine droplet size. The webs inside the annular duct simplify the routing of the duct inside the spray head. It is not necessary to route individual pressurized gas ducts through the whole spray head.

In a preferred embodiment of a spray head and of a spraying device according to the present invention, two component ducts are provided in a housing or in a housing structure. The housing is preferably elongate and narrows in the area of the spray head tip. It can be cylindrical or oval, for example. The component ducts extend parallel to each other in the longitudinal direction of the housing. They open out close to each other at the tip end of the housing at component outlets. At the opposite end, the component ducts open, for example, into inlet openings through which a component can be introduced from a container into the respective component duct. The containers can be, for example, in the form of a double cartridge having two containers, one for each component, in which case the respective container outlets open into the openings on the housing. For discharging the components, the spraying device has a discharge device which, for example, is in the form of a double piston rod, each piston of the double piston rod extending into a respective one of the containers. When the double piston rod is pushed forward, the components from the containers are discharged through the container outlets and are introduced into the component ducts of the spray head.

On the spray head, a cap or sleeve is provided that can be fitted onto the housing with the component ducts. The annular duct for the pressurized gas is formed between an outer wall of the housing and an inner wall of the cap. For this purpose, the cap fits tightly to the housing at one end, and at the other end there is an opening for forming a pressurized gas outlet between the housing and the cap. The housing tip with the component outlets preferably protrudes into the opening of the cap, such that the component outlets come to lie laterally alongside the pressurized gas outlet ducts or even protrude from the cap beyond the pressurized gas outlet ducts in the spraying direction.

In one embodiment, the cap is detachable from the housing, and the pressurized gas supply duct is provided on the cap, for example by a lateral pressurized gas attachment on the cap. The cap can thus be used for different spray heads, i.e. it can be fitted onto the housings of different spray heads. In principle, however, the cap can also be mounted fixedly on the housing, such that it cannot accidentally be separated from the housing.

The webs for forming the pressurized gas outlet ducts in the annular duct are preferably arranged extending radially on the outer wall of the housing. When the cap is fitted onto the housing, the webs bear on the inner wall of the cap, such that pressurized gas outlet ducts separate from one another are formed according to the present invention. However, it is also possible to provide the webs extending radially inward on the inner wall of the cap, such that the webs come to lie on the outer wall of the housing when the cap is fitted. A combination of these possibilities is also conceivable.

In an advantageous embodiment of the present invention, the component outlets at the spray head tip protrude beyond the pressurized gas outlet ducts in the spraying direction. This ensures that mixing of the spray components takes place outside the spray head and, therefore, that the spray head is safeguarded against becoming clogged as a result of the components mixing too early. Two component outlets are preferably provided, which each emerge on a surface of the spray head tip, in which case the respective surfaces enclose an angle between each other such that the component outlets are oriented obliquely outward with respect to the spraying direction. In this arrangement, the component outlets point in different directions, preferably counter to each other. In this way, it is again possible to avoid a situation where mixing takes place too early and, consequently, the spray head becomes clogged. The exit surfaces of the component outlets are accordingly designed tapering toward each other in an arrow shape, such that they form an edge on the spray head tip, which edge forms the most forward point of the tip. The frontmost area of the housing between the component outlets additionally forms a screening means, which screens the two component outlets from each other. During the discharging of the components from the component outlets, this ensures that the components do not come into contact with each other before being atomized. The surfaces are preferably arranged at an angle of 90 degrees to each other. However, they can also be provided at a more acute or a more obtuse angle.

The webs inside the annular duct are preferably arranged in such a way that the pressurized gas outlet ducts are arranged alongside a connecting line of the two component outlets. Accordingly, the emerging pressurized gas is not oriented along the surfaces directly to the component outlets and instead flows laterally into the atomizing area in front of the component outlets. This avoids a situation where a strong stream of pressurized gas, resulting from a vacuum formation, causes the components to be sucked out of the component ducts. It is only when the discharge device for discharging the components out of the containers, and therefore out of the component outlets, is activated that the components are discharged into the atomizing area in front of the spray head tip. This avoids uncontrolled discharge of the components and, therefore, unintentional mixing of the components. In order to arrange the pressurized gas outlet ducts specifically alongside the component outlets in such a way that the pressurized gas does not flow directly over the outlets, the webs in the annular duct can be arranged accordingly. For example, webs are provided in each case on the connecting line of the two ducts.

In another embodiment of the present invention, the interior of the spray head is provided with a substance duct, or a mixing duct for several components, the outlet of which duct opens out from the spray head tip and which is at least partially surrounded by an annular duct according to the invention in the longitudinal direction. Two container outlets from two containers of a double cartridge preferably open into the substance duct or mixing duct, different components being provided in each of the two containers of the double cartridge. In the design as mixing duct, mixing elements are provided between the mouth of the container outlets of the double cartridge and the outlet at the spray head tip. The mixing elements are used to mix the individual components from the double cartridge directly before the mixture is discharged from the spraying device. In a particularly preferred embodiment, the one mixing channel divides, at the tip of the spray head, into two outlets arranged alongside each other. The two outlets are each preferably provided on a surface of the spray head tip, in which case the surfaces enclose an angle with respect to each other, such that the outlets are directed obliquely outward with respect to the spraying direction, as has already been described above.

According to the invention, the annular duct for the pressurized gas, which annular duct at least partially surrounds the substance duct or mixing duct with the mixing element in the longitudinal direction, has a plurality of webs, which divide the annular duct into pressurized gas outlet ducts that are separate from one another. As has already been described, it is advantageous if the pressurized gas outlet ducts are not oriented directly to the angled surfaces with the component outlets and are instead provided to the sides thereof by means of the webs.

It will be noted that the arrangement of the component outlets on mutually angled surfaces of the spray head tip, such that the component outlets point obliquely outward relative to the component ducts in the spraying direction, independently of the presence of an annular duct with webs, as has been described above, represents an advantageous embodiment of a spray head for a spraying device for spraying a substance or a component. Provision is therefore made for independent claims directed to a spray head for a spraying device having at least one substance or component duct, wherein the component duct or ducts open out at the tip of the spray head in at least two component outlets. The spray head comprises at least one pressurized gas duct, opening out of the spray duct at the tip of the spray head, and a pressurized gas supply duct for introducing pressurized gas into the pressurized gas duct(s). It is important that the component outlets each emerge on a surface of the spray head, wherein the surfaces enclose an angle relative to each other such that the component outlets are oriented obliquely outward relative to the spraying direction. In other words, the outlets of the component ducts are oriented radially outward at an angle. The respective surfaces are accordingly provided tapering toward each other in an arrow shape. The component outlets preferably protrude beyond the outlets of the pressurized gas ducts in the spraying direction, and the pressurized gas outlets are arranged next to a connecting line of two component outlets. For example, in the case of one substance duct extending through the spray head, it can divide into two component outlets at the spray head tip. In the case of two component ducts extending separately alongside each other, these can each open into one of the surfaces provided at an angle to each other on the spray head tip.

BRIEF DESCRIPTION OF THE DRAWINGS

Preferred embodiments of the invention are shown in the drawing, which is not to be interpreted as in any way limiting the invention. Features that become apparent from the figures of the drawing are to be understood as belonging to the disclosure of the invention. In the drawing.

Figure 1:
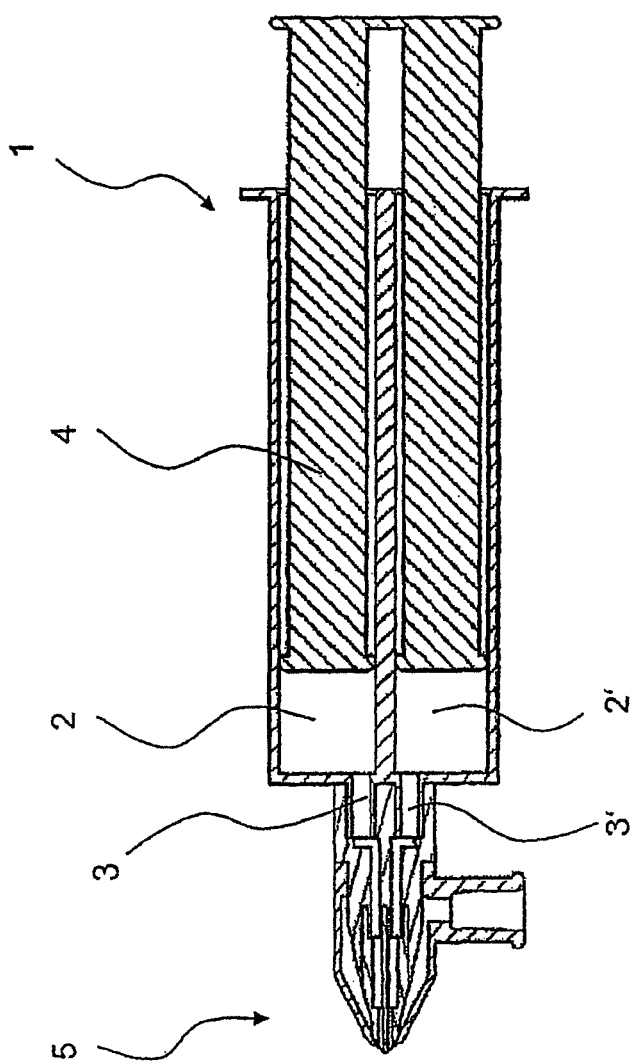
FIG. 1 shows a longitudinal section through a spraying device with a spray head in a first embodiment according to the present invention.

A spraying device and a spray head according to the present invention are shown in a first embodiment in FIG. 1. The spraying device comprises a double syringe 1 with two containers 2 and 2', in each of which a component is provided that is to be sprayed using the spraying device. The containers accommodate, for example, two different components, which form a fibrin adhesive by mixing. The containers 2 and 2' each have a container outlet 3 and 3', respectively. At the end lying opposite the container outlets 3 and 3', the containers 2 and 2' have a discharge device in the form of a double piston 4. When the double piston 4 is advanced into the interior of the containers 2 and 2', the components are discharged from the interior of the containers through the container outlets 3 and 3'. A spray head 5 according to the present invention adjoins the container outlets.

Figure 2:
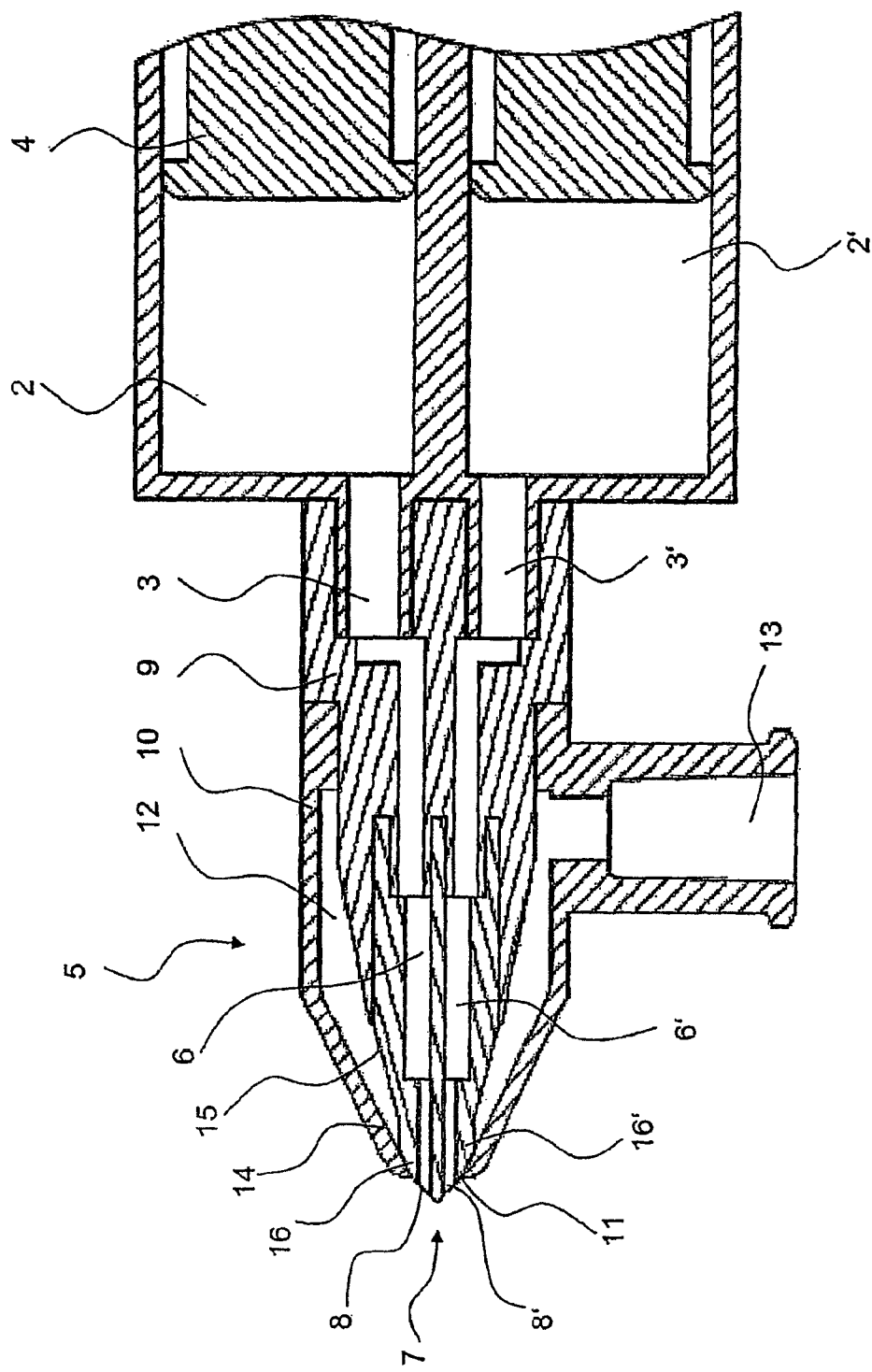
FIG. 2 shows a longitudinal section through the spray head of the spraying device according to the present invention.

The spray head 5 is shown in detail in FIG. 2. In the interior of the spray head, two mutually parallel component ducts 6 and 6' extend alongside each other from an inlet end of the spray head to a spray head tip from which two component outlets 8 and 8' of the component ducts 6 and 6' open out. At the inlet end, the spray head 5 has receiving openings for receiving the container outlets 3 and 3' of the double syringe. The component ducts 6 and 6' are thus joined in fluid connection to the container outlets, such that, when the components are discharged from the containers 2 and 2', the components are discharged through the container outlets 3 and 3' into the component ducts 6 and 6'. The component ducts are accommodated in a housing structure in which the receiving openings for receiving the container outlets are also provided. The container outlets 3 and 3' can be inserted into the openings of the housing structure 9. It is possible to provide a safety mechanism, e.g. in the form of a snap-fit connection, such that the housing structure 9 of the spray head 5 is secured safely on the container outlets 3 and 3' of the double cartridge 1.

A cap 10 is fitted over the housing structure 9, the pushed-on end of the cap 10 bearing tightly on the housing structure 9. For this purpose, a form-fit or force-fit connection can be used for example. It is also possible to provide a seal, for example a sealing ring, between this end of the cap 10 and the housing structure 9. At the opposite end of the cap 10, the latter has an opening 11 from which the area of the housing structure 9 forming the spray head tip 7 protrudes from the cap 10. The area of the housing structure 9 of the spray head tip 7 protrudes from the cap 10 by such a distance that the component outlets 8 and 8' are arranged outside the cap.

Between the cap 10 and the housing structure 9, an annular duct 12 is formed which is provided for receiving a pressurized gas. On one side, the cap 10 has a pressurized gas supply duct 13, through which pressurized gas can be introduced into the annular duct 12. Conventional pressurized gas devices, for example cartridges, can be attached to the pressurized gas supply duct 13. When the cap 10 is fitted onto the housing structure 9, the annular duct 12 is formed between an inner wall 14 of the cap and an outer circumferential wall 15 of the housing structure 9. The housing structure 9 and the cap 10 are designed tapering in the direction of the spray head tip 7. The spray head 5 therefore narrows in the direction of the spray head tip 7. The shape of the cap 10 is adapted to the outer circumferential wall 15 of the housing structure 9 in such a way that the distance between the outer wall 15 of the housing and the inner wall 14 of the cap is small, with the result that the annular duct 12 has a small volume.

In the area of the spray head tip 7, the housing structure 9 has several webs 16 and 16' on its outer circumferential wall 15. The webs touch the inner wall of the cap 10 when the cap 10 is fitted onto the housing structure 9. Between the webs 16, 16', pressurized gas outlet ducts 17 and 17' are formed, which adjoin the annular duct 12 and are separate from one another (see FIG. 4b).

Figure 3:
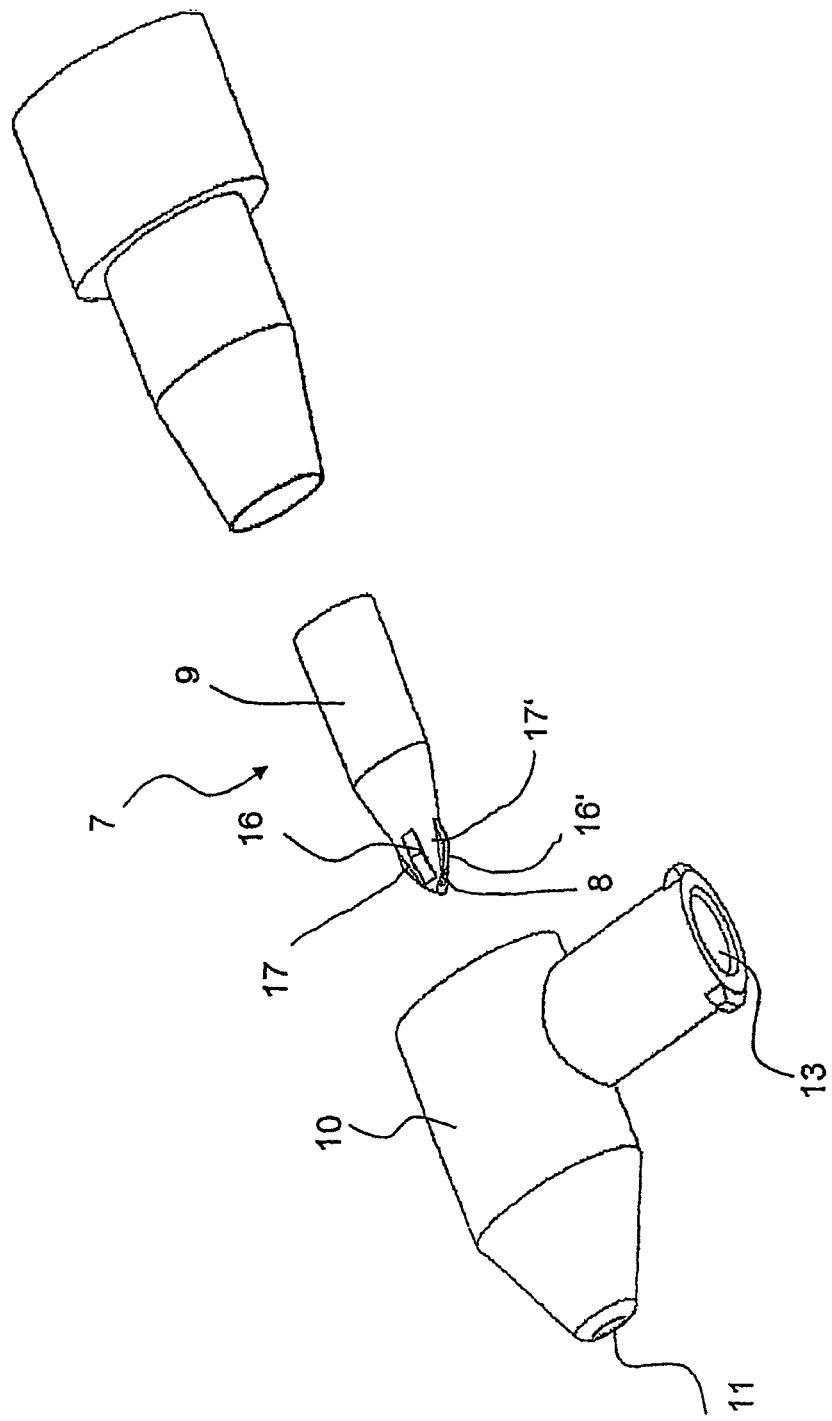
FIG. 3 shows a three-dimensional exploded view of the spray head according to the invention.

FIG. 3 shows the individual elements of the spray head 5 in an exploded view. It will be seen from this that the cap 10 has a cylindrical part, which is adjoined by a conical part whose tip is provided with an opening 11. The pressurized gas supply duct 13 is arranged laterally on the cylindrical part. The housing structure 9 is shown in two parts in the figure. The two parts are joined together to form the housing structure 9. The two-part form of the housing structure makes production of the structure easier. The structure accordingly has a cylindrical part, through which the component ducts extend. The housing structure has a conical shape at one end. The spray head tip 7 is formed in the tip area of the cone. In the area of the spray head tip 7, the housing structure 9 has, on its outer circumferential wall, webs 16 and 16' that extend in the longitudinal direction of the housing structure. When the cap 10 is fitted onto the housing structure 9, the outer surfaces of the webs 16, 16' bear on the inner wall 14 of the cap. The pressurized gas outlet ducts 17, 17' then form between the webs 16, 16'.

Figure 4A:
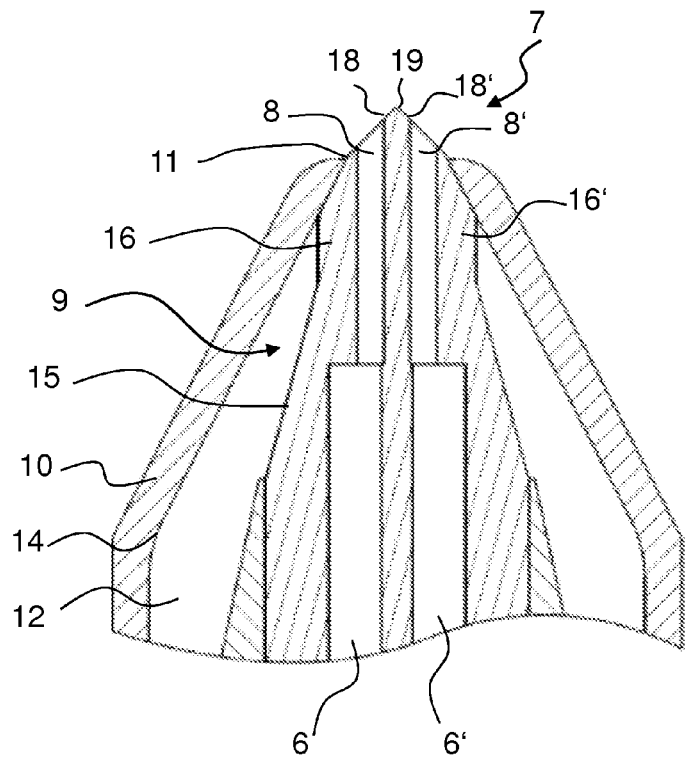
FIG. 4a shows a longitudinal section along a first plane through a spray head tip.
Figure 4B:
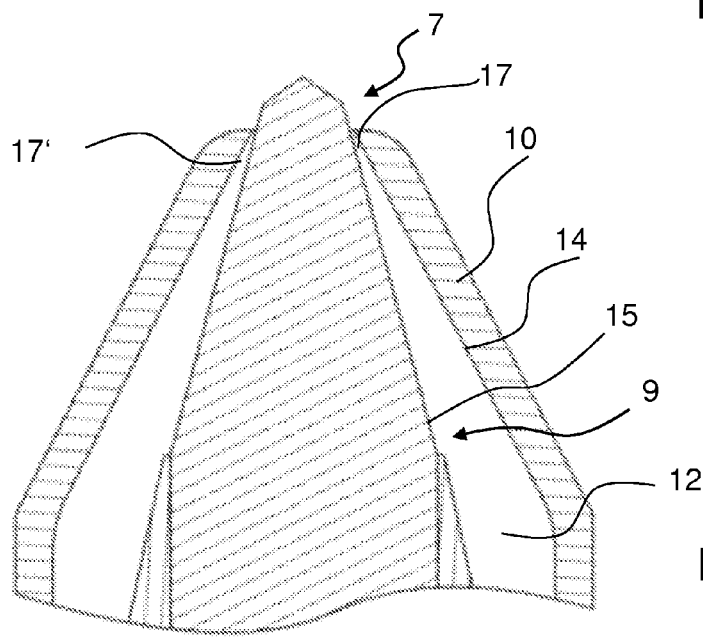
FIG. 4b shows a longitudinal section along a second plane through the spray head tip.

FIGS. 4a and 4b show sections through the spray head tip of the spray head 5. In FIG. 4a, the section runs through two mutually opposite webs 16 and 16' that are provided on the outer wall 15 of the housing. The annular gap 12, which forms between the inner wall 14 of the cap and the outer wall 15 of the housing, is closed in the area of the spray head tip 7, since the webs 16, 16' of the housing structure 9 bear on the inner wall 14 of the cap.

The component outlets 8, 8' of the component ducts 6, 6' open out from the housing structure 9 outside the cap 10, since the tip area of the housing structure 9 protrudes through the opening 11 from the cap 10. The component outlets 8 and 8' are provided on respective surfaces 18, 18' of the housing structure 9 of the spray head that enclose an angle between each other, such that the component outlets 8, 8' are, in relation to the component ducts 6 and 6', oriented obliquely with respect to the spraying direction. In other words, the surfaces 18, 18' of the component outlets 8, 8' are provided obliquely with respect to the longitudinal axis of the component ducts 6, 6' such that the component outlets 8 and 8' eject a component sideways out of the spray head. The two components discharged from the component outlets 8 and 8' are therefore discharged in directions pointing away from each other. Between the two component outlets 8 and 8', the angled surfaces 18 and 18' form a tip 19, which acts as a screening means for the two component outlets 8 and 8'. By virtue of the fact that the components are discharged obliquely to the sides from the component outlets 8 and 8', and also by virtue of the screening means 19 between the component outlets, it is possible to ensure that the individual components do not come into contact with each other directly after exiting the component outlets. This avoids a situation where the spray head or the spray head tip becomes clogged, because of undesired early contact between the components, and spraying of the components is no longer possible. In the embodiment shown, the surfaces 18, 18' are at an angle of approximately 90° to each other. The component outlets 8 and 8' are therefore oriented at a 45° angle to the longitudinal axis of the component ducts 6 and 6'. Other angles are possible, as long as the described function of the angled surfaces is satisfied.

In FIG. 4b, the spray head tip 7 is shown in a sectional plane running through two mutually opposite pressurized gas outlet ducts 17, 17', which are formed between the webs 16, 16'. The cap 10 and the housing structure 9, in the area of the spray head tip 7, are formed tapering conically toward the tip. The longitudinal direction of the pressurized gas outlet ducts 17 and 17' is therefore oriented obliquely with respect to the longitudinal axis of the housing structure 9 or of the component ducts 6 and 6'. The pressurized gas outlet ducts 17 and 17' are therefore focused on a point in front of the spray head tip 7.

It will be seen from FIGS. 4a and 4b that the pressurized gas outlet ducts 17 and 17' do not lie on the connecting line of the two component outlets 8 and 8'. The webs 16 and 16' are provided along the connecting line of the component outlets 8 and 8'. The pressurized gas outlet ducts 17, 17' are not therefore directed to the surfaces 18, 18' that have the component outlets 8 and 8' and are instead arranged alongside the connecting line of the surfaces. The result of this arrangement of the pressurized gas outlet ducts with respect to the component outlets is that no vacuum effect occurs at the component outlets 8 and 8', which effect could cause the components to be sucked out of the component outlets in an uncontrolled manner. The pressurized gas stream is guided laterally past the surfaces 18 and 18', such that the pressurized gas impinges on the components only when the latter have already emerged from the component outlets 8 and 8'. Since the pressurized gas outlet ducts 17, 17' are focussed on a point above the spray head tip, the components are atomized in this area and mixed with each other. Another result of the focussing of the pressurized gas outlet ducts 17, 17' is that the mixed components can be discharged onto an application site in a targeted manner. There is no development of a broad atomizing cone of the kind that occurs in conventional spraying devices.

Figure 4C:
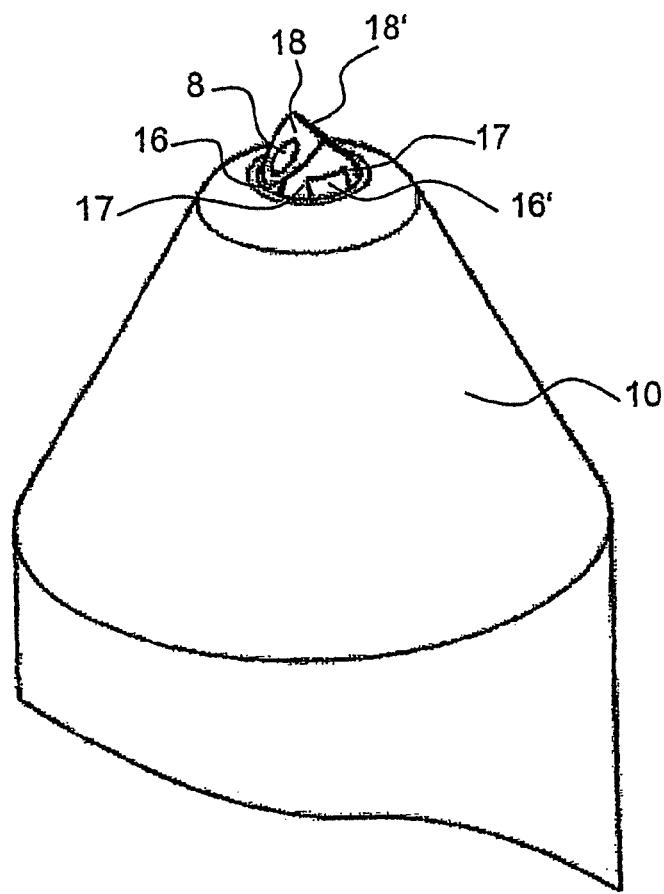
FIG. 4c shows a three-dimensional view of the spray head tip.

FIG. 4c shows a three-dimensional view of the spray head tip, 7 according to the invention. It will be seen from FIG. 4c that the pressurized gas outlet ducts 17, 17' are formed between the webs 16, 16' and are arranged next to or alongside the connecting line of the component outlets 8, 8' or of the surfaces 18, 18'. It will be seen that the component outlets 8 and 8' open out from the housing structure 9 outside the cap 10. In this embodiment, four webs 16, 16' are formed on the circumference of the housing structure 9. The webs are provided on the connecting line of the component outlets 8 and 8' and on the section line of the surfaces 18, 18'. Therefore, pressurized gas outlet ducts 17, 17' are formed on both sides of one of the surfaces 18 and 18'. In other words, two pressurized gas outlet ducts 17, 17' are formed in each case on both sides of the component outlets.

Figure 5A:
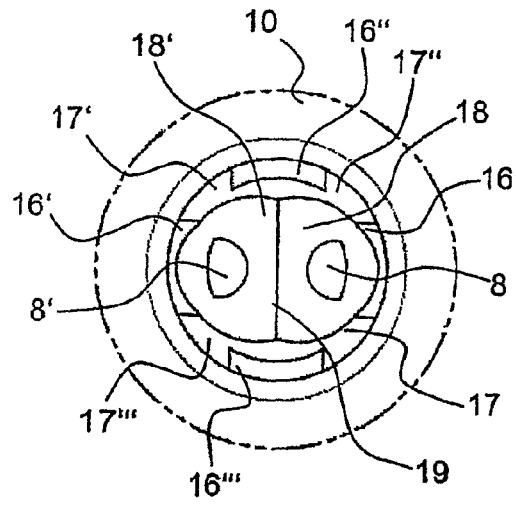
FIG. 5a shows a front view of a spray head tip according to FIG. 4c with two outlet surfaces.

FIGS. 5a to 5d show front views of different embodiments of spray head tips according to the present invention. The spray head tips differ from one another in terms of the number of component outlets and the number of oblique surfaces from which the component outlets open out. FIG. 5a shows a spray head tip according to the embodiment in FIGS. 4a to 4c. Two component outlets 8 and 8' are shown on two surfaces 18 and 18' arranged next to each other. The surfaces 18 and 18' are arranged obliquely with respect to the longitudinal axis of the spray head, in such a way that they form between them an edge, which functions as screening means 19. The spray head tip protrudes from the cap 10 in such a way that four pressurized gas outlet ducts 17, 17', 17" and 17'" form between the webs 16, 16', 16" and 16'". The pressurized gas outlet ducts are arranged in a ring around the component outlets 8 and 8'. Two webs 16 and 16' are arranged with respect to the component outlets 8 and 8' in such a way as to lie on a connecting line of the two component outlets 8 and 8'. The webs 16" and 16'" are arranged alongside this connecting line, or on a line perpendicular to the latter.

Figure 5B:
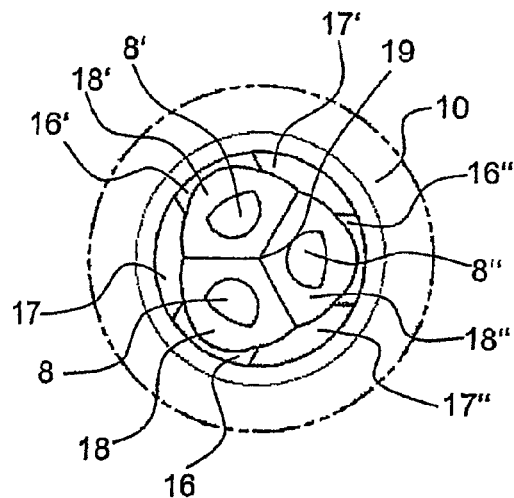
FIG. 5b shows a front view of a spray head tip with three outlet surfaces.

FIG. 5b shows a spray head tip with three component outlets 8, 8' and 8", which open out from three surfaces 18, 18' and 18" arranged obliquely with respect to one another. The component outlets 8, 8' and 8" are arranged in a triangle shape. The three webs 16, 16' and 16" form between them three pressurized gas outlet ducts 17, 17' and 17". The webs come to lie underneath the surfaces 18, 18' and 18". The section lines of the surfaces 18, 18' and 18" meet at the center point of the spray head tip and thus form a tip-like screening means 19.

Figure 5C:
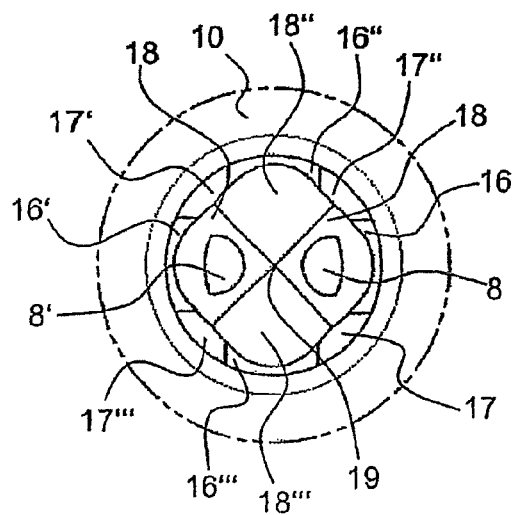
FIG. 5c shows a front view of a spray head tip with four surfaces.
Figure 5D:
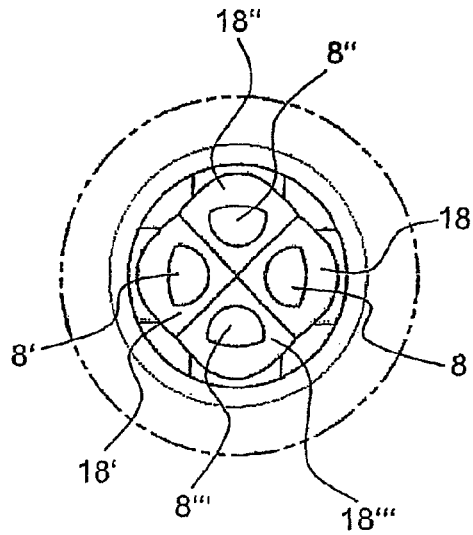
FIG. 5d shows a front view of a spray head tip with four outlet surfaces.

In FIGS. 5c and 5d, four surfaces 18, 18', 18" and 18'" are provided, which extend obliquely with respect to the longitudinal axis of the spray head and whose section lines meet at a point. In FIG. 5c, two component outlets 8 and 8' are provided, which open out from two mutually opposite surfaces 18 and 18'. In FIG. 5d, four component outlets 8, 8', 8" and 8'" are provided, which each open out from one of the surfaces 18, 18', 18" and 18'".

In the illustrative embodiments shown, the surfaces from which the component outlets open out are arranged symmetrically, and their surface normals intersect the longitudinal axis of the spray head. In principle, however, the surfaces can also be asymmetrical, and their surface normals can extend alongside the longitudinal axis of the spray head and their surfaces can also be curved or twisted. The important point is that the component outlets are directed obliquely outward, and the surfaces preferably form between them a screening means.

Figure 6:
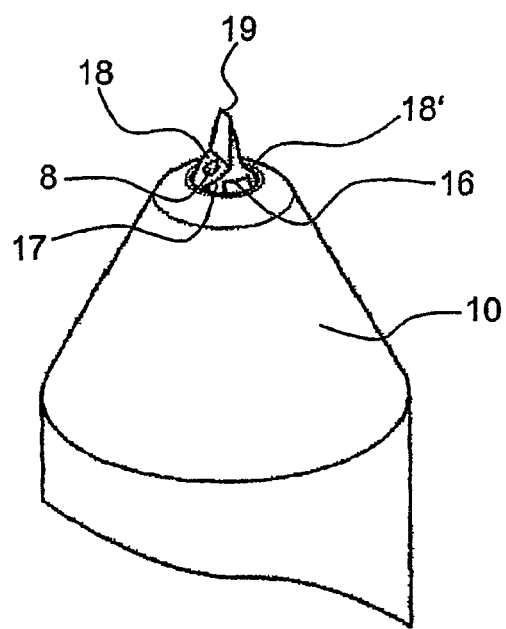
FIG. 6 shows a three-dimensional view of a spray head tip with another embodiment of a screening means.

FIG. 6 shows another illustrative embodiment of a spray head tip with an elongated screening means 19. The screening means 19 protrudes like a plate between the surfaces 18 and 18'. It protrudes substantially from the connecting line, formed by the intersecting surfaces 18 and 18', and forward along the longitudinal axis of the spray head from the spray head tip. Such a screening means, in addition to the obliquely arranged component outlets, avoids an undesirable situation where different components are mixed together too early, and it thus avoids the spray head becoming clogged.

Figure 7:
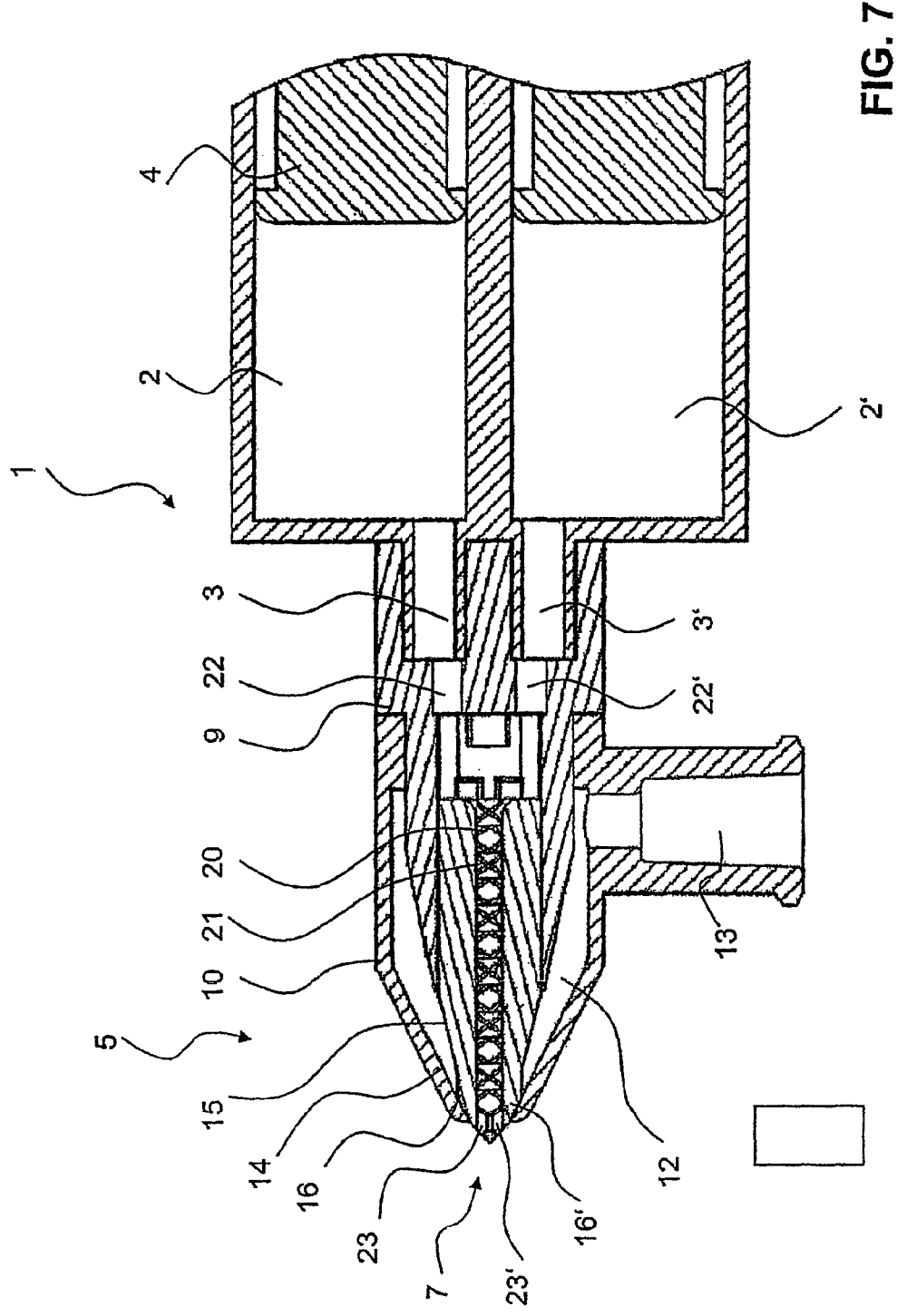
FIG. 7 shows a longitudinal section through a spray head in a second embodiment according to the invention.

FIGS. 7 and 8a to 8c show another embodiment of a spray head and of a spraying device according to the present invention. Structural parts corresponding to the structural parts in the embodiment according to FIGS. 1 to 4 have the same reference signs. FIG. 7 shows the spray head 5 and a portion of the double syringe 1. The double syringe 1 has two containers 2 and 2', which are each adjoined by a container outlet 3 and 3'. In the containers 2 and 2', a double piston 4 is provided as a discharge device for discharging the components from the containers 2 and 2'.

In this embodiment, the housing structure 9 has a component duct 20, which serves as a mixing channel and in which mixing elements 21 are arranged. The housing also has two access ducts 22 and 22', which connect the container outlets 3, 3' to the component duct 20 when the housing structure 9 is fitted over the container outlets 3 and 3' of the double syringe 1. When the two components from the containers 2 and 2' are discharged through the container outlets 3, 3' by means of the double piston 4, they come into contact in the component duct 20, and, when the double piston 4 is pushed further into the containers 2 and 2', the components inside the component duct 20 are advanced along the mixing element 21, as a result of which the two components are mixed together inside the spray head by means of the mixing elements 21. This embodiment is therefore suitable for spraying substances which have to be mixed together just shortly before being used, but which do not rapidly harden in such a way as to clog the component duct or the mixing elements.

The cap 10 with the pressurized gas supply duct 13 is fitted over the housing structure 9, such that the annular duct 12 forms between the housing structure 9 and the cap 10. On the housing structure 9, webs 16 and 16' are arranged on the outer circumference in the area of the spray head tip 7. The webs 16, 16' bear on the inner wall 14 of the cap 10. The component duct 20, in the area of the outlet thereof, is divided by the mixing elements 21 in such a way that two component outlets 23 and 23' arranged next to each other are formed. When the mixture is discharged from the component duct 20, the mixture is therefore ejected through two separate component outlets 23, 23' lying close to each other.

Figure 8A:
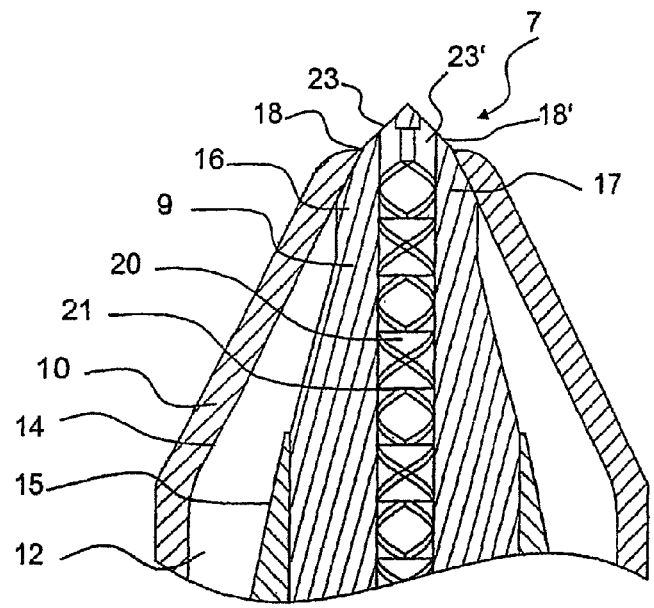
FIG. 8a shows a longitudinal section along a first plane through a spray head tip according to the second embodiment.

FIG. 8a shows a longitudinal section through the spray head tip 7, which longitudinal section runs through two mutually opposite webs 16, 16'. The component duct 20 with the mixing elements 21 is formed in the longitudinal direction inside the housing structure 9. Between the inner wall 14 of the cap 10 and the outer wall 15 of the housing structure 9, the annular duct 12 is formed which, in the area of the tip of the spray head tip 7, is closed by the webs 16, 16' in this sectional plane.

The component outlets 23 and 23' are arranged on two surfaces 18 and 18', which are arranged at an angle to each other. The function of the oblique surfaces 18 and 18' is the same as in the preceding illustrative embodiment.

Figure 8B:
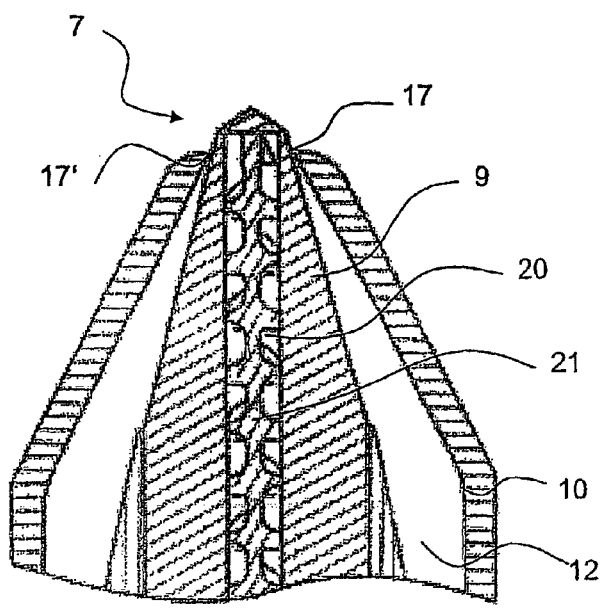
FIG. 8b shows a longitudinal section along a second plane of the spray head tip according to the second embodiment.

FIG. 8b shows a longitudinal section through the spray head tip 7 along a plane between two webs 16 and 16'. The component duct 20 with the mixing elements 21 is shown in the interior of the housing structure 9, which component duct 20 has no outlet in this sectional plane. Between the housing structure 9 and the cap 10, the annular duct 12 is formed which, in the area of the spray head tip 7, opens into the pressurized gas outlet ducts 17 and 17'.

The spray head tip 7 corresponds to the tip shown in the three-dimensional view in FIG. 4c. It will be seen from this that, in the area of the spray head tip, the housing structure protrudes through the opening 11 of the cap 10, such that the component outlets 23 and 23', and the outlets 8 and 8' in FIG. 4c, come to lie outside the cap 10. The webs 16, 16' can be seen on the outer circumference of the housing structure 9. The pressurized gas outlet ducts 17, 17' are arranged between the webs 16, 16'. The surfaces 18, 18' are arranged at an angle to each other and form a screening means 19 between the component outlets 23, 23'.

The design of the pressurized gas line according to the present invention, with an annular duct and with webs arranged therein for controlling and focussing the pressurized gas ejection at the spray head tip of the spraying device, corresponds to that of the illustrative embodiment according to FIGS. 1 to 4. On the one hand, the formation of the webs in the annular duct means that the amount of pressurized gas needed for spraying the components can be reduced, and the stream of pressurized gas can be focussed in a targeted manner and can be arranged in a specific way relative to the component outlets. On the other hand, arranging the component outlets on different surfaces arranged at an angle to each other avoids uncontrolled mixing of the discharged components, and the negative effects of a vacuum forming as the pressurized gas flows past are reduced.

In the description of the invention, spraying direction is to be understood as the direction generally corresponding to the longitudinal axis of the spraying device. However, it is also possible for a substance to be sprayed at an angle to the longitudinal axis of the spraying device. In this case, the normal extending perpendicular to an outlet opening of an annular duct according to the invention can indicate the spraying direction, since a pressurized gas stream, composed of all the streams emanating from all the pressurized gas outlet ducts, runs in this direction.

LIST OF REFERENCE SIGNS 1 double syringe
2, 2' container
3, 3' container outlets
4 double piston
5 spray head
6, 6' component ducts
7 spray head tip
8, 8' component outlets
9 housing structure
10 cap
11 opening
12 annular duct
13 pressurized gas supply duct
14 inner wall of cap
15 outer wall of housing
16, 16' webs
17, 17' pressurized gas outlet ducts
18, 18' surfaces
19 screening means
20 component duct
21 mixing elements
22, 22' access duct
23, 23' component outlets

The invention claimed is:

1. A spray head for a spraying device for spraying at least one substance or component, comprising:
a spray head tip;
at least two component outlets that open out from the spray head tip;
at least one substance or component duct arranged in a longitudinal direction that leads to the component outlets;
an annular duct for a pressurized gas, which annular duct at least partially surrounds the at least one substance or component duct in the longitudinal direction and opens out from the spray head at the spray head tip;
a plurality of webs arranged in the annular duct at least in the area of the spray head tip, the webs dividing the annular duct into pressurized gas outlet ducts that are separate from one another, the webs being arranged in such a manner that the pressurized gas outlet ducts have a width between the webs that narrows in the direction of the spray head tip, the width being measured along a circumferential direction; and
a pressurized gas supply duct for introducing pressurized gas into the annular duct.

2. The spray head as claimed in claim 1, wherein at least two component ducts for different components are provided, each component duct opening out into at least one of said component outlets, and the component outlets of the component ducts open out from the spray head tip alongside each other.

3. The spray head as claimed in claim 1, wherein the pressurized gas outlet ducts have a height, as measured along a radial direction, that decreases in the direction of the spray head tip.

4. The spray head as claimed in claim 1, wherein the at least one substance or component duct is formed in a housing, and the annular duct is formed between an outer wall of the housing and an inner wall of a cap fitted onto the housing, and wherein the cap at one end is closed tightly with the housing and at the other end has an opening.

5. The spray head as claimed in claim 4, wherein the cap is mounted fixedly on the housing.

6. The spray head as claimed in claim 4, wherein the pressurized gas supply duct is provided on the cap.

7. The spray head as claimed in claim 4, wherein the webs are arranged in a radially protruding manner on the inner wall of the cap and/or on the outer wall of the housing.

8. The spray head as claimed in claim 1, wherein a screening means is arranged between said at least two component outlets.

9. The spray head as claimed in claim 1, wherein the at least two component outlets on the spray head tip protrude beyond the pressurized gas outlet ducts in the spraying direction.

10. The spray head as claimed in claim 1, wherein the at least two component outlets each emerge on a surface of the spray head tip, and wherein the surfaces enclose an angle between each other such that the component outlets are directed outward at an inclination with respect to the spraying direction.

11. The spray head as claimed in claim 1, wherein the webs are arranged in such a way that the pressurized gas outlet ducts are arranged next to a connecting line of said component outlets.

12. A spray head for a spraying device for spraying at least one substance or component, the spray head comprising:
a spray head tip having two oblique surfaces that are inclined relative to a longitudinal direction so as to enclose an angle between each other;
two component outlets, each of said component outlets opening out at one of said oblique surfaces;
at least one substance or component duct that leads to the component outlets;
an annular duct for a pressurized gas, which annular duct at least partially surrounds the at least one substance or component duct in the longitudinal direction and opens out from the spray head at the spray head tip;
a plurality of webs arranged in the annular duct at least in the area of the spray head tip, the webs dividing the annular duct into pressurized gas outlet ducts that are separate from one another, the webs being arranged in such a manner that for each of said oblique surfaces one of said webs is arranged adjacent to the respective oblique surface, along a connecting line that connects the component outlets, in such a way that the pressurized gas does not flow directly over the outlets; and
a pressurized gas supply duct for introducing the pressurized gas into the annular duct.

13. The spray head as claimed in claim 12, wherein the oblique surfaces meet at an edge defining a section line, and wherein two of said webs are arranged along said section line on two radially opposing sides of the spray head tip.

14. The spray head as claimed in claim 12, wherein the spray head comprises one single substance duct that opens out into the two component outlets.

15. The spray head as claimed in claim 12, wherein the spray head comprises two component ducts, each of said component ducts opening out into one of said component outlets.

16. A spray head for a spraying device for spraying at least one substance or component in a spraying direction, the spray head comprising:
   a spray head tip having at least three oblique surfaces that are inclined relative to the spraying direction so as to enclose an angle between each other;
   a plurality of component outlets, each of said component outlets opening out at one of said oblique surfaces;
   at least one component duct that leads to the component outlets;
   an annular duct for a pressurized gas, which annular duct at least partially surrounds the at least one component duct in the spraying direction and opens out from the spray head at the spray head tip;
   a plurality of webs arranged in the annular duct at least in the area of the spray head tip, the webs dividing the annular duct into pressurized gas outlet ducts that are separate from one another, said webs being arranged in such a manner that for each of said oblique surfaces one of said webs is arranged underneath the respective oblique surface, in such a way that the pressurized gas does not flow directly over the outlet opening out at said oblique surface; and
   a pressurized gas supply duct for introducing pressurized gas into the annular duct.

17. The spray head as claimed in claim 16, wherein the at least three oblique surfaces are divided by section lines that meet at a center point of the spray head tip.

18. A spray head for a spraying device for spraying a substance, the spray head comprising:
   a spray head tip having at least two oblique surfaces that are inclined relative to a longitudinal direction so as to enclose an angle between each other;
   at least two component outlets, each of said component outlets opening out at one of said oblique surfaces;
   one single substance duct that leads to the at least two component outlets;
   an annular duct for a pressurized gas, which annular duct at least partially surrounds the substance duct in the longitudinal direction and opens out from the spray head at the spray head tip;
   a plurality of webs arranged in the annular duct at least in the area of the spray head tip, the webs dividing the annular duct into pressurized gas outlet ducts that are separate from one another; and
   a pressurized gas supply duct for introducing pressurized gas into the annular duct.

19. The spray head as claimed in claim 18, further comprising a mixing element arranged in the substance duct.

* * * * *